US006596771B2

(12) United States Patent
Georgiev

(10) Patent No.: US 6,596,771 B2
(45) **Date of Patent: *Jul. 22, 2003**

(54) DRUGS FOR TREATING VIRAL INFECTIONS

(75) Inventor: Vassil S. Georgiev, Gaithersburg, MD (US)

(73) Assignee: Schering Corporation, Kenilworth, NJ (US)

(*) Notice: Subject to any disclaimer, the term of this patent is extended or adjusted under 35 U.S.C. 154(b) by 33 days.

This patent is subject to a terminal disclaimer.

(21) Appl. No.: 10/187,094

(22) Filed: Jul. 1, 2002

(65) Prior Publication Data

US 2002/0193443 A1 Dec. 19, 2002

Related U.S. Application Data

(63) Continuation-in-part of application No. 09/895,377, filed on Jul. 2, 2001, now Pat. No. 6,433,016.

(60) Provisional application No. 60/260,878, filed on Jan. 12, 2001.

(51) Int. Cl.$^7$ .......................... A61K 31/16; C07C 311/48

(52) U.S. Cl. .......................................... 514/600; 564/79

(58) Field of Search ............................. 564/79; 514/600

(56) References Cited

U.S. PATENT DOCUMENTS 4,292,305 A * 9/1981 Ali et al. ....................... 424/45

FOREIGN PATENT DOCUMENTS

JP 38-19962 9/1938

OTHER PUBLICATIONS

Ali, et al., *J. Med. Chem.* 25, 1235–1240 (1982).
Appel, et al, *Chem. Ber.* 101, 1743–1745 (1968).
Mariani et al, *Il Farmaco, Ed. Sci.*, 31, 272 (1976).
Schenonone et al, *Il Farmaco, Ed. Sci.* 27, 322 (1972).
Appel, et al, *Chem. Ber.* 95, 1753 (1962).
Farag et al., *Phosphorosu Sulfur*, 40, 247–251 (1991).
Sidwell, et al., *Appl. Microbiology 22*, 747–801 (1971).

* cited by examiner

*Primary Examiner*—Peter O'Sullivan
(74) *Attorney, Agent, or Firm*—Palaiyur S. Kalyanaraman

(57) ABSTRACT

A series of imidodisulfamide derivatives have been prepared and are useful to treat antiviral infections, especially infections caused by orthopox viruses.

68 Claims, No Drawings

DRUGS FOR TREATING VIRAL INFECTIONS

This application claims the benefit of priority from U.S. patent application Ser. No. 09/895,377 filed Jul. 2, 2001, now U.S. Pat. No. 6,433,016, which claims priority from provisional patent application Serial No. 60/260,878 filed Jan. 12, 2001.

BACKGROUND OF THE INVENTION

The present invention relates generally to carbocyclic imidodisulfamides, as well as their alkali salts and N-monophosphates. The compounds of this invention possess broad antiviral activity, especially activity against orthopox viruses.

Ali at al., J. Med. Chem. 25: 1235–1240 (1982) describe a series of N,$N^1$-bis(arylcyclopropyl)imidodisulfamide derivatives having antiallergic activity. Appel and Helwerth, Chem. Ber. 101: 1743–1745 (1968) disclose a bis (cyclohexyl)imidodisulfamide derivative. Yamaguchi and Nakano [Japan. Patent 19,962 (1963)] disclose the ammonium salt of a bis(cyclohexyl)imidodisulfamide derivative.

SUMMARY OF THE INVENTION

In accordance with the invention, there are provided carbocyclic imidodisulfamide compounds of the formula:

$$[R—(CR^2R^3)_nNHSO_2]_2NR^1 \qquad (I)$$

or pharmaceutically acceptable salts or solvates of said compound, wherein: n is a number from 0 to 6, R is a carbocyclic radical selected from the group consisting of adamantyl, norbornyl, cyclooctyl and cyclododecyl, $R^1$ is selected from the group consisting of hydrogen, alkali metal, ammonium cation, and monophosphate moiety, and $R^2$ and $R^3$ can be the same or different and are independently selected from the group consisting of H and lower alkyl, further wherein said carbocyclic radical can be optionally substituted with one or more substituents selected from the group consisting of lower alkyl, F, Cl, Br, $NO_2$ and $CF_3$.

The invention further provides a method for treating a warm blooded animal for viral infections, preferably but not limited to infections caused by orthopox viruses (such as vaccinia virus, cowpox, smallpox, monkeypox, camelpox, etc.) which method comprises administering to such animal an therapeutically effective amount of at least one compound of formula (I).

This invention additionally provides a pharmaceutical composition comprising at least one compound of formula I and at least one pharmaceutically acceptable carrier.

DETAILED DESCRIPTION OF THE INVENTION

In an embodiment, this invention provides imidodisulfonamide compounds of formula I, wherein R, n, $R^1$, $R^2$ and $R^3$ are described above.

$$[R—(CR^2R^3)_nNHSO_2]_2NR^1 \qquad (I)$$

Except where stated otherwise, the following definitions apply throughout the present specification and claims. These definitions apply regardless of whether a term is used by itself or in combination with other terms. Hence the definition of "alkyl" applies to "alkyl" as well as to the "alkyl" portions of "alkoxy", "alkylamino" etc.

As used above, and throughout the specification, the following terms, unless otherwise indicated, shall be understood to have the following meanings:

"Patient" includes both human and other animals.

"Mammal" means humans and other mammalian animals.

"Alkyl" means an aliphatic hydrocarbon group, which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means an alkyl group having about 1 to about 6 carbon atoms in the chain, which may be straight or branched. The term "substituted alkyl" means that the alkyl group may be substituted by one or more substituents which may be the same or different, each substituent being independently selected from the group consisting of halo, alkyl, aryl, -cycloalkyl, cyano, hydroxy, alkoxy, and —C(O)O-alkyl. Non-limiting examples of suitable alkyl groups include methyl, ethyl, n-propyl, isopropyl, n-butyl, and t-butyl.

"Alkenyl" means an aliphatic hydrocarbon group comprising at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means an alkenyl group having about 2 to about 6 carbon atoms in the chain, which may be straight or branched. The term "substituted alkenyl" means that the alkenyl group may be substituted by one or more substituents which may be the same or different, each substituent being independently selected from the group consisting of halo, alkyl, aryl, -cycloalkyl, cyano, and alkoxy. Non-limiting examples of suitable alkenyl groups include ethenyl, propenyl, n-butenyl, and 3-methylbut-2-enyl.

"Aryl" means an aromatic monocyclic or multicyclic ring system comprising about 6 to about 14 carbon atoms, preferably about 6 to about 10 carbon atoms. The aryl group can be unsubstituted or substituted on the ring with one or more substituents which may be the same or different, each being independently selected from the group consisting of alkyl, aryl, OCOalkyl, OCOaryl, $CF_3$, heteroaryl, aralkyl, alkylaryl, hydroxy, alkoxy, aryloxy, halo, nitro and cyano. Non-limiting examples of suitable aryl groups include phenyl and naphthyl. The "aryl" group can also be substituted by linking two adjacent carbons on its aromatic ring via a combination of one or more carbon atoms and one or more oxygen atoms such as, for example, methylenedioxy, ethylenedioxy, and the like.

"Aralkyl" means an aryl-alkyl-group in which the aryl and alkyl are as previously described. Preferred aralkyls comprise a lower alkyl group. Non-limiting examples of suitable aralkyl groups include benzyl, phenethyl and naphthalenylmethyl. The bond to the parent moiety is through the alkyl.

"Alkylaryl" means an alkyl-aryl-group in which the alkyl and aryl are as previously described. Preferred alkylaryls comprise a lower alkyl group. Non-limiting example of a suitable alkylaryl groups is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted on the ring by replacing an available hydrogen on the ring by one or more substituents which may be the same or different, each being independently selected from the group consisting of alkyl, aryl and heteroaryl. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Halo" means fluoro, chloro, bromo or iodo groups. Preferred are fluoro, chloro or bromo, and more preferred are fluoro and chloro.

"Halogen" means fluorine, chlorine, bromine or iodine. Preferred are fluorine, chlorine or bromine, and more preferred are fluorine and chlorine.

"Alkoxy" means an alkyl-O— group in which the alkyl group is as previously described. Non-limiting examples of suitable alkoxy groups include methoxy, ethoxy, n-propoxy and isopropoxy. The alkyl group is linked to an adjacent moiety through the ether oxygen.

The term "optionally substituted" means optional substitution with the specified groups, radicals or moieties.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. The term "prodrug", as employed herein, denotes a compound that is a drug precursor, which, upon administration to a subject, undergoes chemical conversion by metabolic or chemical processes to yield a compound of formula I or a salt and/or solvate thereof. A discussion of prodrugs is provided in T. Higuchi and V. Stella, *Pro-drugs as Novel Delivery Systems* (1987) Volume 14 of the A.C.S. Symposium Series, and in *Bioreversible Carriers in Drug Design,* (1987) Edward B. Roche, ed., American Pharmaceutical Association and Pergamon Press, both of which are incorporated herein by reference thereto.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

"Effective amount" or "therapeutically effective amount" is meant to describe an amount of compound of the present invention effective to treat a mammal (e.g., human) having a disease or condition mediated by orthopox viruses, and thus producing the desired therapeutic effect.

The compound of formula I forms salts which are also within the scope of this invention. Reference to a compound of formula I, herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compound of the formula I may be formed, for example, by reacting a compound of formula I with an amount of acid or base, such as, for example, an equivalent amount, in a medium such as, for example, one in which the salt precipitates or in an aqueous medium followed by lyophilization.

Exemplary acid addition salts include acetates, adipates, alginates, ascorbates, aspartates, benzoates, benzenesulforiates, bisulfates, borates, butyrates, citrates, camphorates, camphorsulfonates, maleates, sulfonates, tartrates and the like. Additionally, acids which are generally considered suitable for the formation of pharmaceutically useful salts from basic pharmaceutical compounds are discussed, for example, by S. Berge et al, *Journal of Pharmaceutical Sciences* (1977) 66(1) 1–19; P. Gould, *International J. of Pharmaceutics* (1986) 33 201–217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, and salts with amino acids such as arginine, lysine and the like. Basic nitrogen-containing groups may be quarternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g. benzyl and phenethyl bromides), and others.

Thus, for example, alkali metal salts may be formed by treating the compounds with aqueous alkaline hydroxide solution such as but not limited to sodium hydroxide and potassium hydroxide.

The compounds of this invention may also be utilized in the form of N-substituted monophosphates. Such derivatives may be formed by treating the compounds 1 with phosphorylating agent such as but not limited to phosphoryl oxychloride, phosphorus trichloride.

All such acid salts and base salts are intended to be pharmaceutically acceptable salts within the scope of the invention and all acid and base salts are considered equivalent to the free forms of the corresponding compounds for purposes of the invention.

Compounds of formula I, and salts, solvates and prodrugs thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate" "prodrug" and the like, is intended to equally apply to the salt, solvate and prodrug of enantiomers, stereoisomers, rotamers, tautomers, racemates or prodrugs of the inventive compounds.

When any variable (e.g., aryl, heterocycle, $R^2$, etc.) occurs more than one time in any constituent or in formula I, its definition on each occurrence is independent of its definition at every other occurrence. Also, combinations of substituents and/or variables are permissible only if such combinations result in stable compounds.

The compounds of the invention may be prepared by reacting an appropriate carbocyclic alkylamine derivative (1) with imidodisulfuryl chloride (2) in the presence of triethylamine (n, R, $R^2$ and $R^3$ are as defined above):

$$2\ R\text{—}(CR^2R^3)_nNH_2 + HN(SO_2Cl)_2 \dashrightarrow$$

1 2

$$[R\text{—}(CR^2R^3)_nNHSO_2]_2NH$$

3

The following carbocyclic alkylamine intermediates (1) are commercially available: tricyclo[3.3.1.1$^{3,7}$]decan-1-amine (1; R=1-adamantyl, n=0); [(tricyclo[3.3.1.1$^{3,7}$]-dec-1-yl)methyl]amine (1; R=1-adamantylmethyl, n=1); tricyclo[3.3.1.1$^{3,7}$]decan-2-amine (1;R=2-adamantyl, n=0); exo-bicyclo[2.2.1]heptan-2-amine (1; R=exo-2-norbornyl, n=0); and endo-bicyclo[2.2.1]heptan-2-amine (1; R=endo-2-norbornyl, n=0).

Tricyclo[3.3.1.1$^{3,7}$]decan-1-ethanamine (1; R=1-adamantyl, n=2) may be prepared according to U.S. Pat. No. 3,534,036 of V. L. Narayanan and F. L. Weisenborn, the entire disclosure of which is incorporated herein by reference.

Tricyclo[3.3.1.1$^{3,7}$]decan-2-ethanamide (1; R=2-adamantyl, n=2) and 2-(tricyclo[3.3.1.13,7]dec-2-ylidene) ethanamine (4):

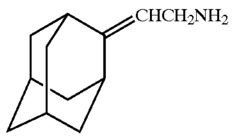

4 were prepared according to the procedure of Mariani and Schenone, II Farmaco, Ed. Sci. 31: 272–276 (1976) and Schenone et al. II Farmaco, Ed. Sci. 27: 322–332 (1972).

Imidodisulfuryl chloride was prepared utilizing the procedure of Appel and Eisenhouer, Chem. Ber. 95: 1753 (1962).

The compounds of the invention may also be prepared as their ammonium salts (6) by reacting an appropriate carbocyclic alkylamine derivative (1) (n, R, $R^2$ and $R^3$ are as defined above) with the ammonium salt of imidodisulfuryl chloride (5) according to the procedures of Appel and Helwerth [Chem. Ber. 101: 1743–1745 (1968)] and Yamaguchi and Nakano [Japan. Patent 19,962 (1963)]:

$$R\text{—}(CR^2R^3)_nNH_2 + (CH_3)_3N^+SO_2N^-SO_2Cl \quad (5)$$

$$[R\text{—}(CR^2R^3)_nNHSO_2]_2N^-][R\text{—}(CH_2)_nN^-NH_3^+] \quad 6$$

In order to increase their solubility in water and saline, the compounds of the invention may also be prepared as their alkali salts (8) by reacting an appropriate carbocyclic imidodisulfamide derivative 3 (n, R, $R^1$, $R^2$ and $R^3$ are defined as above) with aqueous alkaline hydroxide solution such as but not limited to sodium hydroxide and potassium hydroxide:

$$[R\text{—}(CR^2R^3)_nNHSO_2]_2NH + NaOH \dashrightarrow$$

3 7

$$[R\text{—}(CR^2R^3)_n)NHSO_2]_2N^-Na^+$$

8

In order to increase their solubility in water and saline, the compounds of the invention may also be prepared as their N-substituted monophosphate derivatives (10) according to the procedure of Zavlin and Efremov, Phosphorous Sulfur, 40: 247–251 (1991) by reacting an appropriate carbocyclic imidodisulfamide derivative 3 (n, R, $R^2$ and $R^3$ are as defined above) with a phosphorylating agent 9 (e.g., phosphoric anhydride, phosphorus trichloride, phosphorous pentoxide and phosphorous oxychloride):

$$[R\text{—}(CR^2R^3)_nNHSO_2]_2NH + P_4O_{10} \dashrightarrow$$

3 9

$$[R\text{—}(CR^2R^3)_n)NHSO_2]_2N\text{—}P(O)(OH)_2$$

10

By having increased solubility in water and saline, compounds of the formula 6, 8 and 10 may be easily administrated by oral, intranasal, and intraperitoneal routes to treat warm-blooded animals against infections caused by orthopox viruses.

The present invention is illustrated in more detail by reference to the following non-limiting examples.

EXAMPLES

Example 1

N,$N^1$-Bis(tricyclo[3.3.1.$1^{3,7}$]dec-1-yl) imidodisulfamide (3; R=1-adamantyl, n=0)

Under a nitrogen atmosphere, triethylamine (177.71 mL, 1.275 mol) was added over 1.75 hour to a solution of imidodisulfuryl chloride (90.95 g, 0.425 mol) in 2.55 L of anhydrous acetonitrile at −40° C. (dry ice/acetone bath). The resulting yellow solution was stirred at −40° C. for 1 hour and then allowed to warm to 0° C. While stirring rapidly, solid tricyclo[3.3.1.$1^{3,7}$]decan-1-amine (192.84 g, 1.275 mol) was added portionwise over 2 hours at such a rate that allowed the temperature of the reaction mixture to be maintained at −5 to 0° C. for 1 hour, and at room temperature for 18 hours, the insolubles were filtered off and the filtrate evaporated under reduced pressure. The resulting residue and the insolubles were combined and dissolved in 2 L of methanol. The methanolic solution was acidified with 2 equivalents of 2 N hydrochloric acid (490 L), and stirred at ambient temperature for 30 min. After dilution with 2.5 L of water, a precipitate formed. The reaction mixture was filtered off and the crude solid was recrystallized from ethanol providing 105.4 g of white crystalline compound 3 (R=1-adamantyl, n=0). M.p. 210° C. (decomp.).

Anal. Calcd. For $C_{20}H_{33}N_3O_4S_2$: C, 54.15; H, 7.50; N, 9.47; S, 14.45. Found: C, 54.00; H, 7.52; N; 9.55; S, 14.54.

Example 2

Exo-N,$N^1$-Bis(bicyclo[2.2.1]hept-2-yl) imidodisulfamide (3; R=2-norbornyl, n=0)

The compound of the example was prepared by a procedure similar to that described in Example 1 except that exo-bicyclo[2.2.1]heptan-2-amine (1; R=exo-2-norbornyl, n=0) was substituted for tricyclo[3.3.1.$1^{3,7}$]-decan-1-amine. M.p. 208° C. (ethanol).

Anal. Calcd. For $C_{14}H_{25}N_3O_4S_2$: C, 46.26; H, 6.93; N, 11.56; S, 17.64. Found: C, 46.22; H, 6.96; N, 11.51; S, 17.71.

Example 3

Endo-N,$N^1$-Bis(bicyclo[2.2.1]hept-2-yl) imidodisulfamide (3; R=2-norbornyl, n=0)

The compound of this example was prepared by a procedure similar to that described in Example 1 except that endo-bicyclo[2.2.1]heptan-2-amine (1; R=endo-2-norbornyl, n=0) was substituted for tricyclo[3.3.1.$1^{3,7}$]-decan-1-amine, and 5 moles of triethylamine were used instead of 3 moles. M.p. 205–206° C. (ethanol).

Anal. Calcd. For $C_{14}H_{25}N_3O_4S_2$: C, 46.26; H, 6.93; N, 11.56; S, 17.64. Found: C, 46.21; H, 6.94; N, 11.54; S, 17.63.

Example 4

N,$N^1$-Bis[2-(tricyclo[3.3.1.$1^{3,7}$]-dec-1-yl)ethyl] imidodisulfamide (3; R=1-adamantyl, n=2)

The compound of the example was prepared by a procedure similar to that described in Example 1 except that [2-(tricyclo[3.3.1.$1^{3,7}$]dec-1-yl)ethyl]amine (1; R=1-adamantyl, n=2) was substituted for tricyclo[3.3.1.$1^{3,7}$]-decan-1-amine. M.p. 162–164° C. (ethanol).

Anal. Calcd. For $C_{24}H_{41}N_3O_4S_2$: C, 57.68; H, 8.27; N, 8.41; S, 12.83. Found: C, 57.54; H, 8.30; N, 8.32; S, 12.84.

Example 5

N,$N^1$-Bis(tricyclo[3.3.1.$1^{3,7}$]dec-1-yl)methyl] imidodisulfamide (3; R=1-adamantyl, n=1)

The compound of this example was prepared by a procedure similar to that described in Example 1 except that [(tricyclo[3.3.1.$1^{3,7}$]dec-1-yl)methyl]amine (1; R=1-adamantyl, n=1) was substituted for tricyclo[3.3.1.$1^{3,7}$]-decan-1-amine. M.p. 187–190° C. (ethanol).

Anal. Calcd. For $C_{22}H_{37}N_3O_4S_2$: C, 56.02; H, 7.91; N, 8.91; S, 13.59. Found: C, 55.74; H, 8.25; N, 8.83; S, 13.25.

Example 6

N,$N_1$-Bis[2-(tricyclo[3.3.1.$1^{3,7}$]dec-2-yl)ethyl] imidodisulfamide (3; R=2-adamantyl, n=2)

The compound of this example was prepared by a procedure similar to that described in Example 1 except that [2-(tricyclo[3.3.1.$1^{3,7}$]des-2-yl)ethyl]amine (1; R=2-adamantyl, n=2) was substituted for tricyclo[3.3.1.$1^{3,7}$]-decan-1-amine. M.p. 180–181° C. (ethanol).

Anal. Calcd. For $C_{24}H_{41}N_3O_4S_2$: C, 57.68; H, 8.27; N, 8.41; S, 12.83. Found: C, 57.79; H, 8.66; N, 8.40; S, 12.80.

Example 7

N,$N^1$-Bis[2-[(tricyclo[3.3.1.$1^{3,7}$]dec-2-ylidene) ethyl]-imidodisulfamide (11)

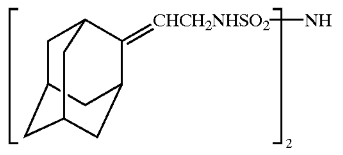

11

The compound of this example was prepared by a procedure similar to that described in Example 1 except that 2-(tricyclo[3.3.1.$1^{3,7}$]dec-2-ylidene)ethanamine (4) was substituted for tricyclo[3.3.1.$1^{3,7}$]decan-1-amine. M.p. 182–183° C. (ethanol).

Anal. Calcd. For $C_{24}H_{37}N_3O_4S_2$: C, 58.15; H, 7.52; N, 8.48; S, 12.94. Found: C, 58.30; H, 7.58; N, 8.48; S, 12.75.

Example 8

N,$N^1$-Di(tricyclo[3.3.1.$1^{3,7}$]dec-2-yl) imidodisulfamide (3; R=2-adamantyl, n=0)

The compound of this example was prepared by a procedure similar to that described in Example 1 except that tricyclo[3.3.1.$1^{3,7}$]decan-2-amine (1; R=2-adamantyl, n=0) was substituted for tricyclo[3.3.1.$1^{3,7}$]decan-1-amine and 5 moles of triethylamine were used instead of 3 moles. M.p. 221–222° C. (decomp.) (2-propanol).

Anal. Calcd. For $C_{20}H_{33}N_3O_4S_2$: C, 54.15; H, 7.50; N, 9.47; S, 14.45. Found: C, 54.62; H, 7.74; N, 9.50; S, 14.06.

Example 9

N,$N^1$-Dicyclooctylimidodisulfamide (3; R= cyclooctyl, n=0)

The compound of the example was prepared by a procedure similar to that described in Example 1 except that cyclooctylamine (1; R=cyclooctyl, n=0) was substituted for tricyclo[3.3.1.$1^{3,7}$]decan-1-amine. M.p. 183–185° C. (ethanol).

Anal. Calcd. for $C_{16}H_{33}N_3O_4S_2$: C, 48.58; H, 8.41; N, 10.62; S, 16.21. Found: C, 48.77; H, 8.78; N, 10.54; S, 15.86.

Example 10

N,$N^1$-Dicyclododecylimidodisulfamide (3; R= cyclododecyl, n=0)

The compound of this example was prepared by a procedure similar to that described in Example 1 except that cyclododecylamine (1; R=cyclododecyl, n=0) was substituted for tricyclo[3.3.1.$1^{3,7}$]decan-1-amine. M.p. 205° C. (ethanol).

Anal. Calcd. For $C_{24}H_{49}N_3O_4S_2$: C, 56.77; H, 9.73; N, 8.28; S, 12.63. Found: C, 56.62; H, 9.60; N, 8.28; S, 12.26.

Example 11

Sodium N,$N^1$(tricyclo[3.3.1.$1^{3,7}$dec-1-yl) imidodisulfamide (1; R=1-adamantyl, n=0, $R^1$= sodium)

N,$N^1$-Bis(tricyclo[3.3.1.$1^{3,7}$]dec-1-yl)imidodisulfamide (200 mg) was suspended in 5 mL of absolute methanol. Then, 1.5 mL of 10 percent aqueous sodium hydroxide solution was added and the reaction mixture was heated slightly in water bath until complete dissolution of the imidodisulfamide 3 (R=1-adamantyl, n=0). After cooling, the resulting sodium salt precipitated as white fluffy crystalline mass. The solvent was stripped under vacuum leaving 200 mg of the sodium salt of 1 (R=1-adamantyl, n=0, $R^1$=sodium). M.p. over 200° C. (water).

Example 12

N,$N^1$(tricyclo[3.3.1.$1^{3,7}$dec-1-yl)imidodisulfamide monophosphate (1; R=1-adamantyl, n=0, $R^1$=P(O) $(OH)_2$)

N,$N^1$-Bis(tricyclo[3.3.1.$1^{3,7}$]dec-1-yl)imidodisulfamide (200 mg; 36 mmol) and 51 mg of phosphoric anhydride ($P_4O_{10}$; 18 mmol) were heated in trichloromethane (10 mL; distilled from phosphoric anhydride) overnight. After evaporation of the solvent, the residue was saturated repeatedly with diethyl ether until the reaction product was obtained as powder. M.p. over 200° C.

Assay for Antiviral Activity

The antiviral activity of the compounds of the invention was determined by several methods through the National Institute of Allergy and Infectious Diseases, NIH Testing Program.

According to the method of Sidwell and Huffman Appl. Microbiol. 22: 797–801 (1971), antiviral activity is determined by using viral cytopathogenic effect (CPE) inhibition in 96-well microplates. Seven concentrations (1,000, 320, 100, 32, 10, 3.2, and 1.0 microgram/mL final concentration in panel cups) of compounds were employed. Compound was added to the cells to be infected 15 minutes before virus exposure. A virus dosage equivalent to the CCID50 was then administered. (The virus concentration which causes 50% cell death, established by titration of a cell monolayer with a homogenate of cultures from 100 virally infected cells). Antiviral activity may be expressed as virus rating (VR) in accordance with Sidwell et al., and as a minimum inhibitory concentration (MIC). Cytotoxicity of each dosage level of compound was evaluated in the same plate using microscopically visible cell anomalies as criterion for evaluation. Included with each test was a known positive compound—ribavirin, sodofovir (HPMPC) and/or cyclic HPMPC may be used as positive controls for RNA viruses. The antiviral test was read approximately 72 hours after addition of virus, at the time when viral CPE reached essentially maximal levels.

In the plaque reduction assay using cowpox virus in cell culture, the compounds of the invention were applied both during and after virus adsorption in order to determine whether compounds were acting as inhibitors of virus adsorption as opposed to an intracellular mode of action. Confluent 6-well plates of monkey(Vero) cells were used. For compound being present during the virus adsorption process, cell medium was aspirated and 2×compound was applied followed by virus diluted to give about 100 plaque forming units (PFU) per well. Compound and virus containing medium were each in a volume of 0.2 mL. Plates were rocked every 5–10 minutes for an hour, after which time the medium was removed and 2.0 mL of 1×compound in MEM/2% Fetal Bovine Serum was applied for three days. For compound being present after the virus adsorption period, 100 PFU of virus per 0.4 mL was rocked on cells for an hour as described above. After that time, the medium was removed and 2.0 mL of 1×compound in MEM/2% fetal Bovine Serum was applied per well for three days. Wells were aspirated and covered with about 1.0 mL/well of 0.1% crystal violet in 10% buffered formalin for 5 minutes. Then, plates were aspirated, rinsed under tap water, and blotted dry. A light box was used to aid in counting the plaques in each well. Sidofovir (HPMPC) and cyclic HPMPC were used as positive controls.

In the cytopathic effect inhibition assay, low passage (3–10) human foreskin fibroblast (HFF) cells are trypsinized, counted, and seeded into 96-well tissue culture plates at a cell concentration of $2.5 \times 10^4$ cells in 0.1 mL of minimal essential medium (MEM) supplemented with 10% fetal bovine serum (FBS). The cells are then incubated for 24 hours at 37° C. in a 5% $CO_2$:95% air, 90% humidified atmosphere. The media is then removed and 100 microliter of MEM containing 2% FBS is added to all but the first row. In the first row, 125 microliter of media containing the compound is added in triplicate wells. Media alone is added to both cell and virus control wells. The compound in the first row of wells is then diluted serially 1:5 throughout the remaining wells by transferring 25 microliter using the Cetus Liquid Handling Machine. The plates are then incubated for 60 minutes and 100 microliter of an appropriate virus concentration added to each well, excluding cell control wells, which received 100 microliter of MEM. In initial experiments, the virus concentration utilized will be 1,000

Plaque Forming Units (PFU) per well. The plates are then incubated at 37° C. in a $CO_2$ incubator for five days. After the incubation period, media is aspirated and the cells stained with a 0.1% crystal violet solution for four days. The stain is then removed and the plates rinsed using tap water until all excess stain is removed. The plates are allowed to dry for 24 hours, and the amount of CPE in each row determined using a Bio Tek Multiplate Autoreader. EC50 and IC50 values are determined by comparing compound-treated and compound-untreated cells using a computer program. (The EC50 value measures compound concentration that inhibits viral replication by 50%; the IC50 value detects compound toxicity to dividing cells by measuring compound concentration that inhibits cell growth by 50%).

In the plaque reduction assay, two days prior to use, HFF cells are plated into six well plates and incubated at 37° C. with 5% $CO_2$ and 90% humidity. On the date of the assay, the compound is made up at 2× the desired concentration in 2×MEM with 5% FBS and then serially diluted 1:5 using six concentrations of compound. The initial concentration is 200 microgram/mL. The compound dilutions are then placed in a 42° C. water bath. The 4% agarose for the overlay is prepared with reagent quality water and microwaved until the agarose has dissolved. This is then placed into the 42° C. water bath to cool. The virus to be used is diluted in MEM containing 10% FBS to a desired concentration, which will give 20–30 plaques per well. The media is then aspirated from the wells and 0.2 microliter of virus is added to each well in triplicate with 0.2 microliter of media being added to compound toxicity wells. The plates are then incubated for one hour with shaking every 15 minutes. After incubation, an equal amount of agarose is added to each compound dilution. Each agarose/compound dilution is then added to the appropriate wells. The assay is incubated for five days, after which the cells are stained with 2.0 microliter per well of 5% neutral red stain for six hours. The stain is then aspirated, and the plaques counted using a stereomicroscope at 10×magnification.

In the cowpox virus plaque assay, in one condition the compound of Example 1 was added to cells 5 minutes before virus adsorption and then continuously for 3 days. In the second condition, virus was adsorbed first for 1 hour, then the compound was added for three days. The compound of Example 1 was found to be equally active under both conditions with an EC50 value in monkey (Vero) cells of 2.0 microgram/mL. At 3.0 microgram/mL, the plaques were nearly completely eliminated, and at 1.0 microgram/mL the plaques were tiny relative to the untreated ones. Cell monolayers were healthy up to 30 microgram/mL (the highest concentration tested). From previous data, sidofovir (HPMPC) is active in these cells at about 12.0 microgram microgram/mL.

In the CPE inhibition assay, the compound of Example 1 showed the following values measuring anti-orthopox virus activities:

(A) Vaccinia Virus (HFF Cells)
EC50: 0.05 microgram/mL;
EC90: 1.40 microgram/mL;
CC50: 77.80 microgram/mL;
DV50: 2.20 microgram/mL;
SI: 1,556

(B) Cowpox Virus (HFF Cells)
EC50: 1.10 microgram/mL;
EC90: 7.30 microgram/mL;
CC50: 77.80 microgram/mL;
CDV50: 3.80 microgram/mL;
CDV90: 13.30 microgram/mL;
SI: 77.8

(CC50 measures the cytotoxic concentration in uninfected cells; The Selectivity Index (SI) measures the compound toxicity and is calculated according to CC50/EC50).

In the plaque reduction assay, the compound of Example 1 showed the following values measuring anti-orthopox virus activities:

(A) Vaccinia Virus (HFF Cells)
EC50: 0.09 microgram/mL;
EC90: 0.15 microgram/ml;
CC50: 100.00 microgram/mL;
CDV50: 50.90 microgram/mL;
CDV90: 19.9 microgram/mL;
SI: 1,111

(B) Cowpox Virus (HFF Cells)
EC50: 0.49 microgram/mL;
EC90: 1.70 microgram/mL;
CC50: 100.0 microgram/mL;
CDV50: 11.70 microgram/mL; CDV90: 18.7 microgram/mL
SI: 204

When tested in the CPE assay against nine variola virus (smallpox) isolates (eight major, and one minor), the compound of Example 1 showed an average EC50 of 0.10 microgram/mL, and CC50 of 43.0 microgram/mL.

In the Neutral Red Uptake Assay (using stationary HFF cells), the compound of Example 1 showed the following values measuring toxicity:

CC50: 78.9 microgram/mL;
ACV CC50: over 100 microgram/mL;

In the CPE inhibition assay, the compound of Example 11 showed the following values measuring anti-orthopox virus activities:

(A) Vaccinia Virus (HFF Cells)
EC50: 0.04 microgram/mL;
EC90: 0.11 microgram/mL
CC50: 65.00 microgram/mL;
CDV EC50: 1.80 microgram/mL;
CDV EC90: 3.7 microgram/mL
SI: 1,625

(B) Cowpox Virus (HFF Cells)
EC50: 0.50 microgram/mL;
EC90: 2.10 microgram/mL
CC50: 65.00 microgram/mL;
CDV EC50: 2.30 microgram/mL
CDV EC90: 3.90 microgram/mL
SI: 130

(CC50 measures the cytotoxic concentration in uninfected cells; The Selectivity Index (SI) measures compound toxicity and is calculated according to CC50/EC50).

In the plaque reduction assay, the compound of Example 11 showed the following values measuring anti-orthopox virus activities:

(A) Vaccinia Virus (HFF Cells)
CC50: 87.60 microgram/mL

In the Neutral Red Uptake Assay (using stationary HFF cells), the compound of Example 11 showed the following values measuring toxicity:

CC50: 87.6 microgram/mL;

ACV CC50: over 100 microgram/mL;

CDV CC50: over 100 microgram/mL

When tested against cowpox infection in female BALB/c mice, an intraperitoneal dose of 100 mg/kg daily of the compound of Example 11 given twice daily for 5 days starting 4 hours before virus challenge significantly reduced the virus titer on Day 3 of measurement as follows:

Lung titer on Day 3: 6.6±1.3 ($P<0.05$)

Saline: 8.0±0.2

The invention further provides a method for treating a warm blooded animal for viral infections, preferably but not limited to infections caused by orthopox viruses (such as vaccinia virus, cowpox, smallpox, monkeypox, camelpox, etc.) which method comprises administering to such animal an therapeutically effective amount of at least one compound of formula (I). The compounds of this invention can be administered to warm-blooded animals perorally, parenterally, topically or intranasally as active ingredients in customary dosage unit compositions. These dosage unit compositions contain the active ingredient and at least one inert pharmaceutical carrier. Dosage unit forms contemplated by the present invention include tablets, capsules, solutions, suspensions, aerosols, and parenteral compositions such as intramuscular, intravenous or intradermal preparations. Sustained release dosage forms are also contemplated where the active ingredient is bound to an exchange resin that, optionally, can be coated with a diffusion barrier coating to modify the release properties of the resin.

The quantity of active ingredient administered in such dosage forms can vary over a wide range depending upon the mode of administration, the size and weight of the patient and whether the nature of the treatment is prophylactic or therapeutic in nature. In general, dosage unit forms containing from about 1.0 mg to 250 mg of the active ingredient. In humans, the dose is administered from 1 to 4 times daily. The total daily dosage will be from about 5.0 mg to 1,000 mg, although lower or higher amounts can be used. A preferred total daily dose would be from 10 mg to 100 mg of active ingredient.

In another embodiment, this invention discloses pharmaceutical compositions comprising the imidodisulfamide compounds of the present invention. For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, $18^{th}$ Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 100 mg, preferably from about 1 mg to about 50 mg, more preferably from about 1 mg to about 25 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 300 mg/day, preferably 1 mg/day to 50 mg/day, in two to four divided doses.

The present invention may be embodied in other specific forms without departing from the spirit or essential attributes thereof and, accordingly, reference should be made to the appended claims, rather than to the foregoing specifications, as indicating the scope of the invention.

What is claimed is:

1. A compound having a formula $$[R—(CR^2R^3)_nNHSO_2]_2NR^1 \quad (I)$$

or pharmaceutically acceptable salts, solvates or isomers of said compound or salts or solvates of said isomers, wherein:

n is a number from 0 to 6,

R is a carbocyclic radical selected from the group consisting of adamantyl, norbornyl, cyclooctyl and cyclododecyl, $R^1$ is selected from the group consisting of hydrogen, alkali metal, ammonium cation, and monophosphate moiety, and $R^2$ and $R^3$ can be the same or different and are independently selected from the group consisting of H and lower alkyl, further wherein said carbocyclic radical can be optionally substituted with one or more substituents selected from the group consisting of lower alkyl, F, Cl, Br, $NO_2$ and $CF_3$.

2. The compound of claim 1, wherein n is 0 to 2.

3. The compound of claim 1, wherein said alkali metal is sodium or potassium.

4. The compound of claim 1, wherein $R^1$ is hydrogen.

5. The compound of claim 1, wherein $R^2$ and $R^3$ are the same and are both hydrogen.

6. The compound of claim 1, wherein $R^2$ and $R^3$ are different.

7. The compound of claim 1, wherein said substituent on said carbocyclic radical is F, $NO_2$, $CF_3$, Cl or Br.

8. The compound of claim 1, wherein said substituent on said carbocyclic radical is a lower alkyl.

9. $N,N^1$-Bis(tricyclo[3.3.1.$1^{3,7}$]dec-1-yl) imidodisulfamide, a compound according to claim 1.

10. exo-$N,N^1$-Bis(bicyclo[2.2.1]hept-2-yl) imidodisulfamide, a compound according to claim 1.

11. endo-$N,N_1$-Bis(bicyclo[2.2.1]hept-2-yl) imidodisulfamide, a compound according to claim 1.

12. $N,N^1$-Bis[2-(tricyclo[3.3.1.$1^{3,7}$]dec-1-yl)ethyl] imidodisulfamide, a compound according to claim 1.

13. $N,N^1$-Bis[(tricyclo[3.3.1.$1^{3,7}$]dec-1-yl)methyl] imidodisulfamide, a compound according to claim 1.

14. $N,N^1$-Bis[2-(tricyclo[3.3.1.$1^{3,7}$]dec-2-yl)ethyl] imidodisulfamide, a compound according to claim 1.

15. $N,N^1$-Bis[2-(tricyclo[3.3.1.$1^{3,7}$]dec-2-ylidene)ethyl] imidodisulfamide, a compound according to claim 1.

16. $N,N^1$-Di(tricyclo[3.3.1.$1^{3,7}$]dec-2-yl) imidodisulfamide, a compound according to claim 1.

17. $N,N^1$-Dicyclooctylimidodisulfamide, a compound according to claim 1.

18. $N,N^1$-Dicyclododecylimidodisulfamide, a compound according to claim 1.

19. $N,N^1$-Bis(tricyclo[3.3.1.$1^{3,7}$]dec-1-yl) imidodisulfamide sodium salt ($R^1$=Na), a compound according to claim 1.

20. exo-$N,N^1$-Bis(bicyclo[2.2.1]hept-2-yl) imidodisulfamide sodium salt ($R^1$=Na), a compound according to claim 1.

21. endo-$N,N^1$-Bis(bicyclo[2.2.1]hept-2-yl) imidodisulfamide sodium salt ($R^1$=Na), a compound according to claim 1.

22. $N,N^1$-Bis[2-(tricyclo[3.3.1.$1^{3,7}$]dec-1-yl)ethyl] imidodisulfamide sodium salt ($R^1$=Na), a compound according to claim 1.

23. $N,N^1$-Bis[(tricyclo[3.3.1.$1^{3,7}$]dec-1-yl)methyl] imidodisulfamide sodium salt ($R^1$=Na), a compound according to claim 1.

24. $N,N^1$-Bis[2-(tricyclo[3.3.1.$1^{3,7}$]dec-2-yl)ethyl] imidodisulfamide sodium salt ($R^1$=Na), a compound according to claim 1.

25. $N,N^1$-Bis[2-(tricyclo[3.3.1.$1^{3,7}$]dec-2-ylidene)ethyl] imidodisulfamide sodium salt ($R^1$=Na), a compound according to claim 1.

26. $N,N^1$-Di(tricyclo[3.3.1.$1^{3,7}$]dec-2-yl) imidodisulfamide sodium salt ($R^1$=Na), a compound according to claim 1.

27. $N,N^1$-Dicyclooctylimidodisulfamide sodium salt ($R^1$=Na), a compound according to claim 1.

28. $N,N^1$-Dicyclododecylimidodisulfamide sodium salt ($R^1$=Na), a compound according to claim 1.

29. $N,N^1$-Bis(tricyclo[3.3.1.$1^{3,7}$]dec-1-yl) imidodisulfamide monophosphate [$R^1$=P(O)$(OH)_2$], a compound according to claim 1.

30. exo-$N,N^1$-Bis(bicyclo[2.2.1]hept-2-yl) imidodisulfamide monophosphate [$R^1$=P(O)$(OH)_2$], a compound according to claim 1.

31. endo-$N,N_1$-Bis(bicyclo[2.2.1]hept-2-yl) imidodisulfamide monophosphate [$R^1$=P(O)$(OH)_2$], a compound according to claim 1.

32. $N,N^1$-Bis[2-(tricyclo[3.3.1.$1^{3,7}$]dec-1-yl)ethyl] imidodisulfamide monophosphate [$R^1$=P(O)$(OH)_2$], a compound according to claim 1.

33. $N,N^1$-Bis[(tricyclo[3.3.1.$1^{3,7}$]dec-1-yl)methyl] imidodisulfamide monophosphate [$R^1$=P(O)$(OH)_2$], a compound according to claim 1.

34. $N,N^1$-Bis[2-(tricyclo[3.3.1.$1^{3,7}$]dec-2-yl)ethyl] imidodisulfamide monophosphate [$R^1$=P(O)$(OH)_2$], a compound according to claim 1.

35. $N,N^1$-Bis[2-(tricyclo[3.3.1.$1^{3,7}$]dec-2-ylidene)ethyl] imidodisulfamide monophosphate [$R^1$=P(O)$(OH)_2$], a compound according to claim 1.

36. $N,N^1$-Di(tricyclo[3.3.1.$1^{3,7}$]dec-2-yl) imidodisulfamide monophosphate [$R^1$=P(O)$(OH)_2$], a compound according to claim 1.

37. $N,N^1$-Dicyclooctylimidodisulfamide monophosphate [$R^1$=P(O)$(OH)_2$], a compound according to claim 1.

38. $N,N^1$-Dicyclododecylimidodisulfamide monophosphate [$R^1$=P(O)$(OH)_2$], a compound according to claim 1.

39. A method for treating a warm-blooded animal for infections caused by orthopox viruses, which comprises administering to said animal a therapeutically effective amount of a compound according to claim 1.

40. The method of claim 39, wherein said orthopox virus is vaccinia virus, cowpox, smallpox, monkeypox or camelpox.

41. The method according to claim 39 wherein the compound is $N,N^1$-bis(tricyclo[3.3.1.$1^{3,7}$]dec-1-yl) imidodisulfamide.

42. The method according to claim 40 wherein the compound is exo-$N,N^1$-bis(bicyclo[2.2.1]hept-2-yl) imidodisulfamide.

43. The method according to claim 40 wherein the compound is endo-$N,N^1$-bis(bicyclo[2.2.1]hept-2-yl) imidodisulfamide.

44. The method according to claim 40 wherein the compound is $N,N^1$-bis[2-(tricyclo[3.3.1.$1^{3,7}$]dec-1-yl)ethyl] imidodisulfamide.

45. The method according to claim 40 wherein the compound is $N,N^1$-bis[(tricyclo[3.3.1.$1^{3,7}$]dec-1-yl)methyl] imidodisulfamide.

46. The method according to claim 40 wherein the compound is $N,N^1$-bis[2-(tricyclo[3.3.1.$1^{3,7}$]dec-2-yl)ethyl] imidodisulfamide.

47. The method according to claim 40 wherein the compound is $N,N^1$-bis[2-(tricyclo[3.3.1.$1^{3,7}$]dec-2-ylidene) ethyl]imidodisulfamide.

48. The method according to claim 40 wherein the compound is $N,N^1$-di(tricyclo[3.3.1.$1^{3,7}$]dec-2-yl) imidodisulfamide.

49. The method according to claim 40 wherein the compound is N,N[1]-dicyclooctylimidodisulfamide.

50. The method according to claim 40 wherein the compound is N,N[1]-dicyclododecylimidodisulfamide.

51. The method according to claim 40 wherein the compound is N,N[1]-bis(tricyclo[3.3.1.1$^{3,7}$]dec-1-yl) imidodisulfamide sodium salt ($R^1$=Na).

52. The method according to claim 40 wherein the compound is exo-N,N[1]-bis(bicyclo[2.2.1]hept-2-yl) imidodisulfamide sodium salt ($R^1$=Na).

53. The method according to claim 40 wherein the compound is endo-N,N[1]-bis(bicyclo[2.2.1]hept-2-yl) imidodisulfamide sodium salt ($R^1$=Na).

54. The method according to claim 40 wherein the compound is N,N[1]-bis[2-(tricyclo[3.3.1.1$^{3,7}$]dec-1-yl)ethyl] imidodisulfamide sodium salt ($R^1$=Na).

55. The method according to claim 40 wherein the compound is N,N[1]-bis[(tricyclo[3.3.1.1$^{3,7}$]dec-1-yl)methyl] imidodisulfamide sodium salt ($R^1$=Na).

56. The method according to claim 40 wherein the compound is N,N[1]-bis[2-(tricyclo[3.3.1.1$^{3,7}$]dec-2-yl)ethyl] imidodisulfamide sodium salt ($R^1$=Na).

57. The method according to claim 40 wherein the compound is N,N[1]-bis[2-(tricyclo[3.3.1.1$^{3,7}$]dec-2-ylidene) ethyl]imidodisulfamide sodium salt ($R^1$=Na).

58. The method according to claim 40 wherein the compound is N,N[1]-di(tricyclo[3.3.1.1$^{3,7}$]dec-2-yl) imidodisulfamide sodium salt ($R^1$=Na).

59. The method according to claim 40 wherein the compound is N,N[1]-dicyclooctylimidodisulfamide sodium salt ($R^1$=Na).

60. The method according to claim 40 wherein the compound is N,N[1]-dicyclododecylimidodisulfamide sodium salt ($R^1$=Na).

61. The method of claim 40, wherein said administration is oral, parenteral, subcutaneous, intranasal or intravenous.

62. The method of claim 61, wherein said administration is oral.

63. A pharmaceutical composition comprising at least one compound of claim 1 with at least one pharmaceutically acceptable carrier.

64. A process for preparing a compound of the formula $$[R—C(R^2R^3)_nNHSO_2]_2NH$$

comprising reacting a compound of the formula $R—C(R^2R^3)_nNH_2$ with $HN(SO_2Cl)_2$ in the presence of triethylamine, wherein:

n is a number from 0 to 6,

R is a carbocyclic radical selected from the group consisting of adamantyl, norbornyl, cyclooctyl and cyclododecyl, and $R^2$ and $R^3$ can be the same or different and are independently selected from the group consisting of H and lower alkyl, further wherein said carbocyclic radical can be optionally substituted with one or more substituents selected from the group consisting of lower alkyl, F, Cl, Br, $NO_2$ and $CF_3$.

65. The process for preparing a compound of the formula $$[R—C(R^2R^3)_nNHSO_2]_2N^-Me^+$$

comprising reacting a compound of the formula $[R—C(R^2R^3)_nNHSO_2]_2NH$ with aqueous alkaline hydroxide solution MeOH wherein:

n is a number from 0 to 6,

R is a carbocyclic radical selected from the group consisting of adamantyl, norbornyl, cyclooctyl and cyclododecyl, Me is sodium hydroxide or potassium hydroxide, and $R^2$ and $R^3$ can be the same or different and are independently selected from the group consisting of H and lower alkyl, further wherein said carbocyclic radical can be optionally substituted with one or more substituents selected from the group consisting of lower alkyl, F, Cl, Br, $NO_2$ and $CF_3$.

66. A process for preparing a compound of the formula $$[R—C(R^2R^3)_nNHSO_2]_2N—P(O)(OH)_2$$

comprising reacting a compound of the formula $[R—C(R^2R^3)_nNHSO_2]_2NH$ with a phosphorylating agent in organic solvent, wherein:

n is a number from 0 to 6,

R is a carbocyclic radical selected from the group consisting of adamantyl, norbornyl, cyclooctyl and cyclododecyl, and $R^2$ and $R^3$ can be the same or different and are independently selected from the group consisting of H and lower alkyl, further wherein said carbocyclic radical can be optionally substituted with one or more substituents selected from the group consisting of lower alkyl, F, Cl, Br, $NO_2$ and $CF_3$.

67. The process of claim 66, wherein said phosphorylating agent is selected from the group consisting of phosphoric anhydride, phosphorous trichloride, phosphorous pentoxide and phosphorous oxychloride.

68. The process of claim 66, wherein said organic solvent is trichloromethane, toluene or benzene.

* * * * *